United States Patent
O'Phelan et al.

(10) Patent No.: US 7,190,569 B2
(45) Date of Patent: Mar. 13, 2007

(54) IMPLANTABLE HEART MONITORS HAVING CAPACITORS WITH ENDCAP HEADERS

(75) Inventors: Michael J. O'Phelan, Oakdale, MN (US); Robert R. Tong, Valencia, CA (US); Luke J. Christenson, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/736,209

(22) Filed: Dec. 15, 2003

(65) Prior Publication Data

US 2004/0193221 A1 Sep. 30, 2004

Related U.S. Application Data

(62) Division of application No. 09/706,515, filed on Nov. 3, 2000, now Pat. No. 6,684,102.

(51) Int. Cl.
   *H01G 9/04* (2006.01)
(52) U.S. Cl. ............... 361/509; 361/508; 361/512; 361/523; 361/528; 361/534; 29/25.03
(58) Field of Classification Search ........ 361/523–528, 361/529–534, 508–512, 502–504, 301.3; 29/25.03, 25.01
   See application file for complete search history.

(56) References Cited

U.S. PATENT DOCUMENTS

| | | | |
|---|---|---|---|
| 1,747,486 A | 11/1923 | Macpherson | |
| 1,931,043 A | 10/1933 | Taylor | |
| 3,555,326 A * | 6/1951 | Doughty, Jr | 361/275.1 |
| 3,150,301 A * | 9/1964 | Schils et al. | 361/307 |
| 3,182,238 A | 5/1965 | Toder et al. | |
| 3,424,857 A | 1/1969 | Miller et al. | |
| 3,643,168 A | 2/1972 | Manicki | 325/459 |
| 3,686,538 A | 8/1972 | Webster | |
| 3,723,926 A | 3/1973 | Thomas | 335/268 |
| 3,742,938 A | 7/1973 | Stern | |

(Continued)

FOREIGN PATENT DOCUMENTS

JP    52-004051    1/1977

(Continued)

OTHER PUBLICATIONS

O'Phelan, M. J., et al., "Batteries Including a Flat Plate Design", U.S. Appl. No. 10/360,551, filed Feb. 7, 2003, 121 pgs.

(Continued)

*Primary Examiner*—Nguyen T. Ha
(74) *Attorney, Agent, or Firm*—Schwegman, Lundberg, Woessner & Kluth

(57) ABSTRACT

Implantable heart-monitoring devices, such as defibrillators, pacemakers, and cardioverters, detect abnormal heart rhythms and automatically apply corrective electrical therapy, specifically one or more bursts of electric charge, to abnormally beating hearts. Critical parts in these devices include the capacitors that store and deliver the bursts of electric charge. Some devices use cylindrical aluminum electrolytic capacitors which include terminals that extend from one end of the case, making the capacitor longer and generally necessitating use of larger device housings. Accordingly, the inventors devised capacitor connection structures that allow size reduction. One exemplary capacitor includes two conductive endcaps at opposite ends of its capacitive element, instead of two upright terminals at one end, thereby allowing reduction in the height or volume of the capacitor and/or increases in the dimensions of other components, such as aluminum foils. Other aspects of the invention include heart-monitoring devices that incorporate these capacitors.

28 Claims, 5 Drawing Sheets

U.S. PATENT DOCUMENTS

| | | | |
|---|---|---|---|
| 3,777,570 A | 12/1973 | Thomas | 73/398 |
| 3,803,457 A | 4/1974 | Yamamoto | 317/230 |
| 3,826,143 A | 7/1974 | Thomas et al. | 73/398 C |
| 3,828,227 A | 8/1974 | Millard et al. | 317/230 |
| 3,859,574 A | 1/1975 | Brazier | 317/230 |
| 3,914,666 A | 10/1975 | Schmickl | |
| 3,938,228 A | 2/1976 | Kemkers et al. | 29/25.42 |
| 3,993,508 A | 11/1976 | Erlichman | |
| 4,047,790 A | 9/1977 | Carino | 439/720 |
| 4,086,148 A | 4/1978 | Badia | |
| 4,088,108 A | 5/1978 | Hager | 123/148 CC |
| 4,131,935 A | 12/1978 | Clement | 361/433 |
| 4,169,003 A | 9/1979 | Dangel et al. | |
| 4,171,477 A | 10/1979 | Funari | |
| 4,232,099 A | 11/1980 | Sullivan | |
| 4,247,883 A * | 1/1981 | Thompson et al. | 361/540 |
| 4,307,142 A | 12/1981 | Blitstein et al. | |
| 4,394,713 A | 7/1983 | Yoshida | 361/502 |
| 4,425,412 A | 1/1984 | Dittmann et al. | |
| 4,481,083 A | 11/1984 | Ball et al. | 204/38 A |
| 4,539,999 A | 9/1985 | Mans | |
| 4,553,304 A | 11/1985 | Fleuret | |
| 4,571,662 A | 2/1986 | Conquest et al. | 361/306 |
| 4,604,260 A | 8/1986 | Shimizu et al. | |
| 4,614,194 A | 9/1986 | Jones et al. | |
| 4,616,655 A | 10/1986 | Weinberg et al. | |
| 4,659,636 A | 4/1987 | Suzuki et al. | |
| 4,664,116 A | 5/1987 | Shaya et al. | |
| 4,683,516 A | 7/1987 | Miller | |
| 4,745,039 A | 5/1988 | Yoshinaka | |
| 4,763,229 A | 8/1988 | Ohtuka et al. | |
| 4,782,340 A | 11/1988 | Czubatyj et al. | 340/825.83 |
| 4,796,638 A | 1/1989 | Sasaki | |
| 4,833,719 A | 5/1989 | Carme et al. | |
| 4,843,518 A | 6/1989 | Okumura | |
| 4,931,899 A | 6/1990 | Pruett | |
| 4,970,626 A | 11/1990 | Kakinoki et al. | |
| 5,131,388 A | 7/1992 | Pless et al. | 128/419 D |
| 5,142,439 A | 8/1992 | Huggett et al. | |
| 5,173,375 A | 12/1992 | Cretzmeyer et al. | |
| 5,175,067 A | 12/1992 | Taylor et al. | |
| 5,195,019 A | 3/1993 | Hertz | |
| 5,279,029 A | 1/1994 | Burns | |
| 5,306,581 A | 4/1994 | Taylor et al. | |
| 5,367,437 A | 11/1994 | Anderson | |
| 5,369,547 A | 11/1994 | Evans | |
| 5,414,588 A | 5/1995 | Barbee, Jr. et al. | |
| 5,422,200 A | 6/1995 | Hope et al. | |
| 5,428,499 A | 6/1995 | Szerlip et al. | |
| 5,439,760 A | 8/1995 | Howard et al. | |
| 5,448,997 A | 9/1995 | Kruse et al. | |
| 5,469,325 A | 11/1995 | Evans | |
| 5,471,087 A | 11/1995 | Buerger, Jr. | 257/532 |
| 5,493,259 A | 2/1996 | Blalock et al. | |
| 5,493,471 A | 2/1996 | Walther et al. | |
| 5,507,966 A | 4/1996 | Liu | |
| 5,522,851 A | 6/1996 | Fayram | 607/5 |
| 5,527,346 A | 6/1996 | Kroll | |
| 5,554,178 A | 9/1996 | Dahl et al. | 607/122 |
| 5,559,667 A | 9/1996 | Evans | |
| 5,584,890 A | 12/1996 | MacFarlane et al. | 29/25.03 |
| 5,628,801 A | 5/1997 | MacFarlane et al. | 29/25.03 |
| 5,634,938 A | 6/1997 | Swanson et al. | |
| 5,640,756 A | 6/1997 | Brown et al. | |
| 5,645,586 A | 7/1997 | Meltzer | |
| 5,658,319 A | 8/1997 | Kroll | |
| 5,660,737 A | 8/1997 | Elias et al. | 216/6 |
| 5,691,079 A | 11/1997 | Daugaard | |
| 5,716,729 A | 2/1998 | Sunderland et al. | |
| 5,737,181 A | 4/1998 | Evans | |
| 5,738,104 A | 4/1998 | Lo et al. | |
| 5,754,394 A | 5/1998 | Evans et al. | 361/516 |
| 5,759,394 A | 6/1998 | Rohrbach et al. | |
| 5,774,261 A | 6/1998 | Omori et al. | |
| 5,776,632 A | 7/1998 | Honegger | |
| 5,779,699 A | 7/1998 | Lipson | 606/41 |
| 5,779,891 A | 7/1998 | Andelman | 210/198.2 |
| 5,790,368 A | 8/1998 | Naito et al. | |
| 5,800,724 A | 9/1998 | Habeger et al. | 216/35 |
| 5,801,917 A | 9/1998 | Elias | |
| 5,811,206 A | 9/1998 | Sunderland et al. | |
| 5,814,082 A | 9/1998 | Fayram et al. | |
| 5,855,995 A | 1/1999 | Haq et al. | |
| 5,867,363 A | 2/1999 | Tsai et al. | |
| 5,882,362 A | 3/1999 | Muffoletto et al. | |
| 5,901,867 A | 5/1999 | Mattson | |
| 5,908,151 A | 6/1999 | Elias | 228/110.1 |
| 5,922,215 A | 7/1999 | Pless et al. | 216/6 |
| 5,926,357 A | 7/1999 | Elias et al. | 361/302 |
| 5,926,362 A | 7/1999 | Muffoletto et al. | |
| 5,930,109 A | 7/1999 | Fishler | 361/508 |
| 5,950,131 A | 9/1999 | Vilmur | |
| 5,963,418 A | 10/1999 | Greenwood, Jr. et al. | 361/508 |
| 5,968,210 A | 10/1999 | Strange et al. | 29/25.03 |
| 5,973,906 A | 10/1999 | Stevenson et al. | 361/302 |
| 5,982,609 A | 11/1999 | Evans | |
| 5,983,472 A | 11/1999 | Fayram et al. | 29/25.42 |
| 6,002,969 A | 12/1999 | Machek et al. | 607/122 |
| 6,004,692 A | 12/1999 | Muffoletto et al. | |
| 6,006,133 A | 12/1999 | Lessar et al. | 607/5 |
| 6,009,348 A | 12/1999 | Rorvick et al. | 607/5 |
| 6,030,480 A | 2/2000 | Face, Jr. et al. | |
| 6,032,075 A | 2/2000 | Pignato et al. | 607/5 |
| 6,040,082 A | 3/2000 | Haas et al. | 429/163 |
| 6,042,624 A | 3/2000 | Breyen et al. | 29/25.03 |
| 6,052,625 A | 4/2000 | Marshall | 607/122 |
| 6,094,339 A | 7/2000 | Evans | |
| 6,094,788 A | 8/2000 | Farahmandi et al. | 25/24.41 |
| 6,099,600 A | 8/2000 | Yan et al. | 29/25.03 |
| 6,104,961 A | 8/2000 | Conger et al. | 607/122 |
| 6,110,233 A | 8/2000 | O'Phelan | 29/25.03 |
| 6,110,321 A | 8/2000 | Day et al. | |
| 6,117,194 A | 9/2000 | Strange et al. | 29/25.03 |
| 6,118,651 A | 9/2000 | Mehrotra et al. | 361/509 |
| 6,118,652 A | 9/2000 | Casby et al. | 361/517 |
| 6,139,986 A | 10/2000 | Kurokawa et al. | |
| 6,141,205 A | 10/2000 | Nutzman et al. | 361/509 |
| 6,157,531 A | 12/2000 | Breyen et al. | 361/519 |
| 6,162,264 A | 12/2000 | Miyazaki et al. | |
| 6,184,160 B1 | 2/2001 | Yan et al. | 438/800 |
| 6,191,931 B1 | 2/2001 | Paspa et al. | 361/302 |
| 6,212,063 B1 | 4/2001 | Johnson et al. | 361/517 |
| 6,225,778 B1 | 5/2001 | Hayama et al. | |
| 6,249,423 B1 | 6/2001 | O'Phelan | 361/502 |
| 6,249,709 B1 | 6/2001 | Conger et al. | 607/122 |
| 6,256,542 B1 | 7/2001 | Marshall et al. | 607/126 |
| 6,259,954 B1 | 7/2001 | Conger et al. | 607/122 |
| 6,275,371 B1 | 8/2001 | Yoshio et al. | |
| 6,275,372 B1 * | 8/2001 | Vassallo et al. | 361/511 |
| 6,275,729 B1 | 8/2001 | O'Phelan | 607/5 |
| 6,297,943 B1 | 10/2001 | Carson | 361/500 |
| 6,299,752 B1 | 10/2001 | Strange et al. | 205/152 |
| 6,321,114 B1 | 11/2001 | Nutzman et al. | 607/5 |
| 6,324,049 B1 | 11/2001 | Inagawa et al. | 361/502 |
| 6,326,587 B1 | 12/2001 | Cardineau et al. | 219/121.68 |
| 6,375,688 B1 | 4/2002 | Akami et al. | |
| 6,380,577 B1 * | 4/2002 | Cadwallader | 257/298 |
| 6,388,284 B2 | 5/2002 | Rhodes et al. | |
| 6,388,866 B1 | 5/2002 | Rorvick et al. | 361/503 |
| 6,402,793 B1 | 6/2002 | Miltich et al. | 29/25.03 |
| 6,404,619 B1 | 6/2002 | Marshall et al. | 361/526 |
| 6,409,776 B1 | 6/2002 | Yan et al. | |
| 6,413,283 B1 | 7/2002 | Day et al. | |
| 6,442,015 B1 | 8/2002 | Niiori et al. | 361/502 |

| | | |
|---|---|---|
| 6,451,073 B1 | 9/2002 | Farahmandi et al. ........ 29/25.03 |
| 6,477,037 B1 | 11/2002 | Nielsen et al. .............. 361/520 |
| 6,477,404 B1 | 11/2002 | Yonce et al. |
| 6,493,212 B1 | 12/2002 | Clarke et al. ................ 361/521 |
| 6,509,588 B1 | 1/2003 | O'Phelan et al. |
| 6,522,525 B1 | 2/2003 | O'Phelan et al. |
| 6,571,126 B1 | 5/2003 | O'Phelan et al. |
| 6,585,152 B2 | 7/2003 | Farahmandi et al. |
| 6,628,505 B1 | 9/2003 | Andelman .................. 361/541 |
| 6,674,634 B2 | 1/2004 | O'Phelan et al. ........... 361/509 |
| 6,684,102 B1 | 1/2004 | O'Phelan et al. .............. 607/5 |
| 6,687,118 B1 | 2/2004 | O'Phelan et al. ........... 361/508 |
| 6,699,265 B1 | 3/2004 | O'Phelan et al. .............. 607/1 |
| 6,709,946 B2 | 3/2004 | O'Phelan et al. ........... 438/396 |
| 6,763,265 B2 | 7/2004 | O'Phelan et al. |
| 6,833,987 B1 | 12/2004 | O'Phelan |
| 6,985,351 B2 | 1/2006 | O'Phelan et al. |
| 6,999,304 B2 | 2/2006 | Schmidt et al. |
| 7,072,713 B2 | 7/2006 | O'Phelan et al. |
| 2003/0072124 A1 | 4/2003 | O'Phelan et al. |
| 2003/0077509 A1 | 4/2003 | Probst et al. |
| 2003/0195568 A1 | 10/2003 | O'Phelan et al. .............. 607/5 |
| 2004/0019268 A1 | 1/2004 | Schmidt et al. |
| 2004/0114311 A1 | 6/2004 | O'Phelan et al |
| 2004/0127952 A1 | 7/2004 | O'Phelan et al. |
| 2004/0147960 A1 | 7/2004 | O'Phelan et al. |
| 2004/0147961 A1 | 7/2004 | O'Phelan et al. |
| 2004/0173835 A1 | 9/2004 | Schmidt et al. |
| 2004/0174658 A1 | 9/2004 | O'Phelan et al. |
| 2004/0193221 A1 | 9/2004 | O'Phelan et al. |
| 2004/0215281 A1 | 10/2004 | O'Phelan et al. |
| 2005/0010253 A1 | 1/2005 | O'Phelan et al. |
| 2005/0017888 A1 | 1/2005 | Sherwood et al. |
| 2006/0009801 A1 | 1/2006 | Schmidt et al. |
| 2006/0162887 A1 | 7/2006 | Schmidt et al. |

FOREIGN PATENT DOCUMENTS

| | | |
|---|---|---|
| JP | 59-083772 | 5/1984 |
| WO | WO-98/27562 | 6/1998 |
| WO | WO-99/51302 | 10/1999 |
| WO | WO-9951302 A1 | 10/1999 |
| WO | WO-00/19470 | 4/2000 |
| WO | WO-2006002148 A1 | 1/2006 |

OTHER PUBLICATIONS

O'Phelan, Michael, et al., "Capacitor Having a Feedthrough Assembly with a Coupling Member", U.S. Appl. No. 10/846,805, filed May 14, 2004, 39 pgs.

O'Phelan, M. J., et al., "Capacitor Having a Feedthrough Assembly with a Coupling Member", U.S. Appl. No. 09/706,579, filed Nov. 3, 2000, 29 pgs.

O'Phelan, M. J., et al., "Flat Capacitor for an Implantable Medical Device", U.S. Appl. No. 10/758,701, filed Jan. 15, 2004, 219 pgs.

O'Phelan, M. J., et al., "Flat Capacitor for an Implantable Medical Device", U.S. Appl. No. 10/756,677, filed Jan. 15, 2004, 219 pgs.

O'Phelan, Michael J., "Flat Capacitor Having an Active Case", U.S. Appl. No. 09/706,517, filed Nov. 3, 2000, 39 pgs.

O'Phelan, M. J., et al., "Flat Capacitor having Staked Foils and Edge-Connected Connection Members", U.S. Appl. No. 10/728,655, filed Dec. 5, 2003, 65 pgs.

O'Phelan, M. J., et al., "Implantable Heart Monitors Having Capacitors with Endcap Headers", U.S. Appl. No. 10/736,209, filed Dec. 15, 2003, 19 pgs.

O'Phelan, M. J., et al., "Implantable Heart Monitors Having Flat Capacitors with Curved Profiles", U.S. Appl. No. 10/729,424, filed Dec. 4, 2003, 28 pgs.

Schmidt, Brian L., et al., "Configurations and Methods for Making Capacitor Connections", U.S. Appl. No. 09/706/576, filed Nov. 3, 2000, 26 pgs.

Moynihan, J. D., "Theory, Design and Application of Electrolytic Capacitors", Copyright by John D. Moynihan, (1982), 136 p.

O'Phelan, Michael J., "Flat Capacitor Having an Active Case", U.S. Appl. No. 10/969,441, filed Oct. 20, 2004, 44 pgs.

Shams. A. M., et al., "Titanium hydride formation from Arabian Gulf water", *Desalination, vol. 107*, (1996), 265-276.

* cited by examiner

IMPLANTABLE HEART MONITORS HAVING CAPACITORS WITH ENDCAP HEADERS

CROSS-REFERENCE TO RELATED APPLICATIONS

This application is a division of U.S. patent application Ser. No. 09/706,515, filed on Nov. 3, 2000 now U.S. Pat. No. 6,684,102, the specification of which is incorporated herein by reference.

This application is related to commonly assigned application Ser. No. 09/706,447, filed on Nov. 3, 2000, entitled FLAT CAPACITOR FOR AN IMPLANTABLE MEDICAL DEVICE, which is incorporated herein by reference in its entirety.

FIELD OF THE INVENTION

The present invention concerns capacitors, particularly wet-electrolytic capacitors used in implantable medical devices, such as implantable defibrillators, cardioverters, and pacemakers.

The present invention concerns implantable heart monitors, such as defibrillators and cardioverters, particularly structures and methods for capacitors in such devices.

BACKGROUND

Since the early 1980s, thousands of patients prone to irregular and sometimes life-threatening heart rhythms have had miniature heart monitors, particularly defibrillators and cardioverters, implanted in their bodies. These devices detect onset of abnormal heart rhythms and automatically apply corrective electrical therapy, specifically one or more bursts of electric current, to hearts. When the bursts of electric current are properly sized and timed, they restore normal heart function without human intervention, sparing patients considerable discomfort and often saving their lives.

The typical defibrillator or cardioverter includes a set of electrical leads, which extend from a sealed housing into the walls of a heart after implantation. Within the housing are a battery for supplying power, monitoring circuitry for detecting abnormal heart rhythms, and a capacitor for delivering bursts of electric current through the leads to the heart.

The capacitor is often times a cylindrical aluminum wet electrolytic capacitor. This type capacitor usually includes stacked strips of aluminum foil and paper rolled, or wound, to form a cylindrical structure which is housed in a round tubular aluminum can. The can has an integral aluminum bottom end and an open top end sealed with a non-conductive flat circular lid, known as a header. Two terminals extend from the header, each connected to one of the rolled aluminum foils.

One problem the inventors recognized with these cylindrical capacitors is the overall height of the capacitor, measured from the bottom of the tubular aluminum can to the top of the terminals extending from the header. In particular, the terminals are rigid metal structures that generally require clearance space to avoid contacting other components within the housing of the implantable devices. Providing this clearance space ultimately increases the size of implantable devices beyond that otherwise necessary. Another related problem is that the diameter of the header has a practical minimum of about twelve millimeters and thus restricts how small capacitors and thus implantable devices can be made. Accordingly, the inventors identified a need to develop space-efficient techniques and structures for providing terminals on electrolytic capacitors.

SUMMARY OF THE INVENTION

To address this and other needs, the inventors devised wet electrolytic capacitors with unique connection structures. One exemplary capacitor includes two conductive endcaps at opposite ends of its capacitive element, instead of two upright terminals at one end, thereby allowing reduction in the height or volume of the capacitor and/or increases in the dimensions of other components, such as aluminum foils. Another exemplary capacitor includes two feedthrough assemblies at opposite ends of the wound capacitive element to also facilitate reduction in the height or volume of the capacitor or increasing its energy-storage density.

Other aspects of the invention include an implantable heart monitor, such as a pacemaker, defibrillator, congestive-heart-failure (CHF) device, or cardioverter defibrillator, that incorporates one or more capacitors with the unique connection structures.

DESCRIPTION OF THE PREFERRED EMBODIMENTS

The following detailed description, which references and incorporates FIGS. 1–5, describes and illustrates one or more specific embodiments of the invention. These embodiments, offered not to limit but only to exemplify and teach, are shown and described in sufficient detail to enable those skilled in the art to implement or practice the invention. Thus, where appropriate to avoid obscuring the invention, the description may omit certain information known to those of skill in the art.

Figure 1:
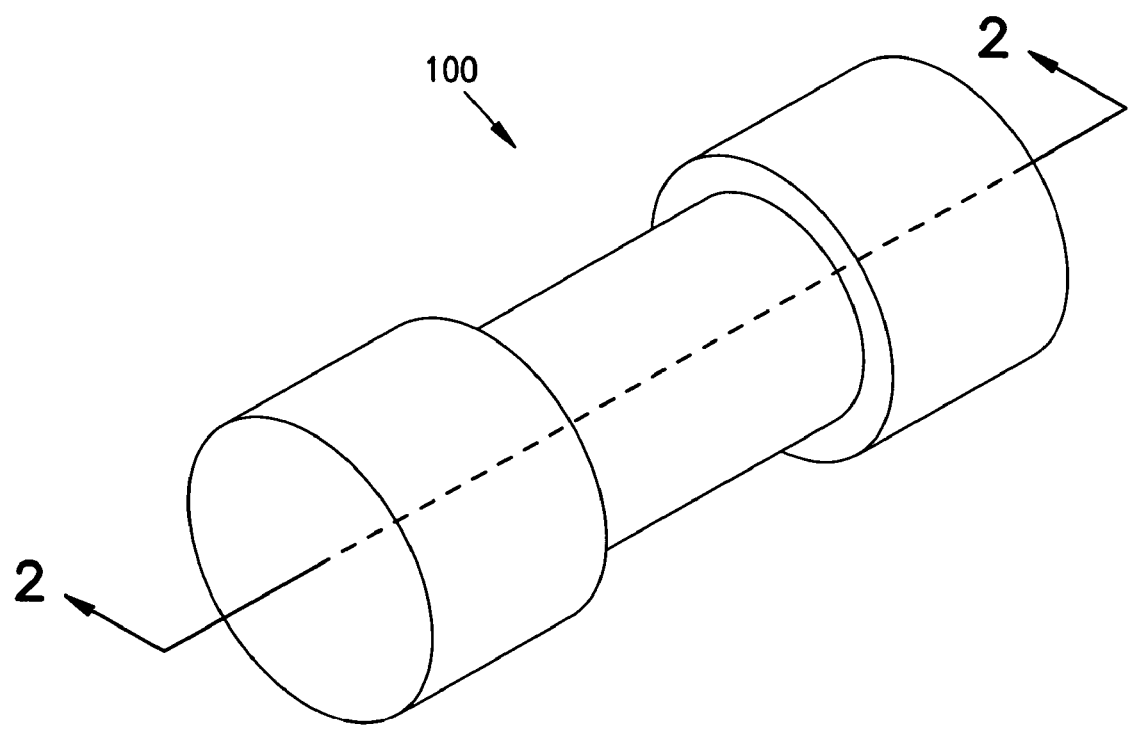
FIG. 1 is a perspective view of an exemplary cylindrical wet electrolytic capacitor 100 embodying teachings of the present invention.
Figure 2:
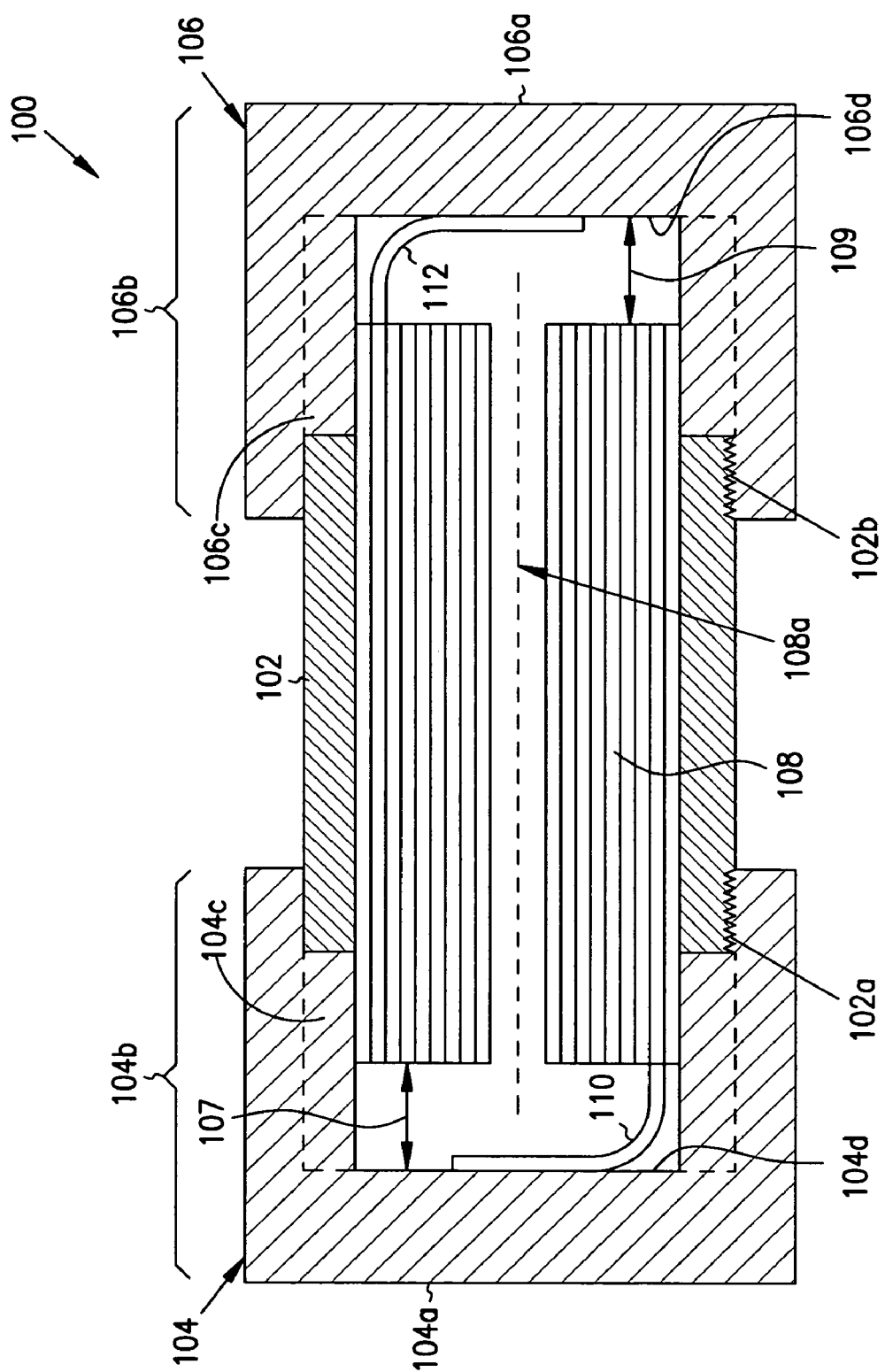
FIG. 2 is a cross-sectional view of capacitor 100 in FIG. 1 taken along line 2—2.

FIG. 1 shows a perspective view of an exemplary cylindrical wet electrolytic capacitor 100 which embodies teachings of the present invention. And, FIG. 2 shows a cross-section of capacitor 100 taken along line 2—2.

In particular, capacitor 100 includes a cylindrical or tubular section 102, cylindrical endcaps 104 and 106, a cylindrical capacitive element 108, anode tab 110, and cathode tab 112. Tubular section 102, which comprises a non-conductive material, such as a ceramic, a polymer, or a plastic, in the exemplary embodiment, at least partially encloses a central portion of wound or rolled capacitive element 108. To fully enclose capacitive element 108, section 102 has two opposing ends 102a and 102b that mate respectively with conductive end caps 104 and 106.

Endcaps 104 and 106, which are exemplarily formed of diecast (deep drawn) or machined aluminum or other conductive metal compatible with the capacitive element, are generally hemispherical or concave (cup-like) in structure, comprising respective planar end portions 104a and 106a and respective annular or tubular portions 104b and 106b. Tubular portions 104b and 106b have respective interior annular shoulders 104c and 106c, which abut respective ends 102a and 102b of tubular section 102, and also allow portions 104b and 106b to overlap corresponding portions of section 102. Thus, in this exemplary embodiment portions 104b and 106b mate with section 102 via a compound butt and lap joint. However, other embodiments omit annular shoulders 104c and 106c, and include threads on the interior of portions 104b and 106b and on the exterior of corresponding portions section 102. Other embodiments use other complementary joint structures and/or adhesives, epoxies, or other sealing compounds.

Endcap 104 is coupled via anode tab 110 to one or more anodic layers within capacitive element 108, and endcap 106 is coupled via cathode tab 112 to a second conductive layer within the capacitive element. More particularly, anode tab 110 contacts an interior surface 104d of endcap 104, and cathode tab 112 contacts an interior surface 106d of endcap 106. Interior surfaces 104d and 106d are separated by respective distances 107 and 109 from capacitive element 108 to prevent the tabs from shorting with other parts of the capacitive element.

In the exemplary embodiment, tabs 110 and 112 are welded respectively to surfaces 104d and 106d, and distances 107 and 109 are both approximately 0.02 inches (0.508 millimeters.) Some embodiments attach the tabs using conductive adhesives. Other embodiments reduce one or both of distances 107 and 109 by increasing the end margins of separators in capacitive element 108 and/or placing one or more insulative inserts between surface 104d and the capacitive element or between surface 106d and the capacitive element.

Figure 3:
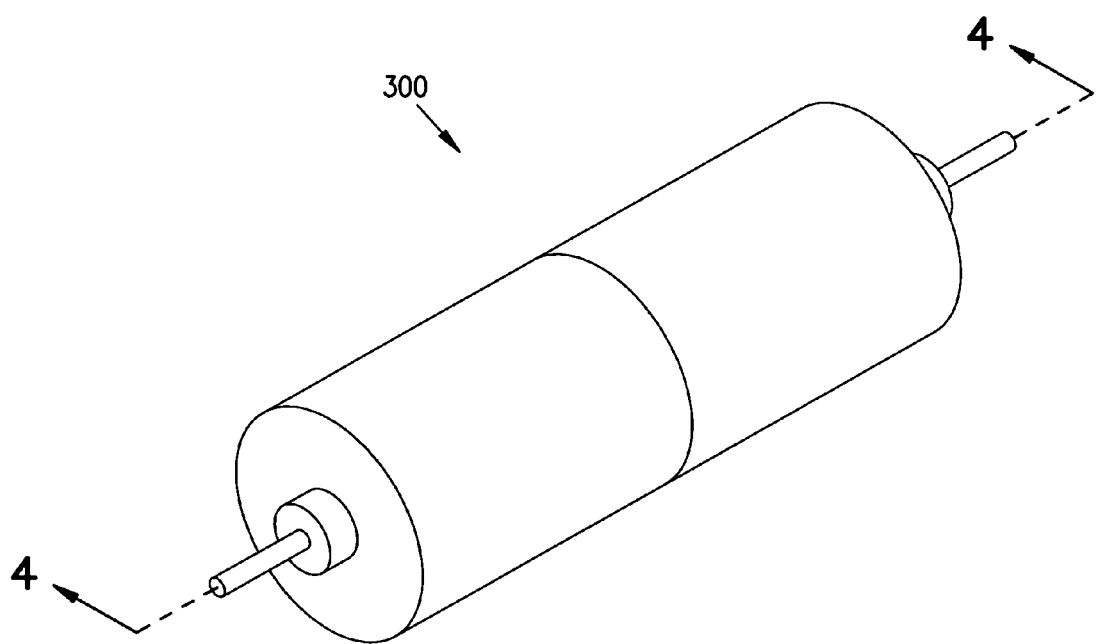
FIG. 3 is a perspective view of an exemplary cylindrical wet electrolytic capacitor 300 embodying teachings of the present invention.
Figure 4:
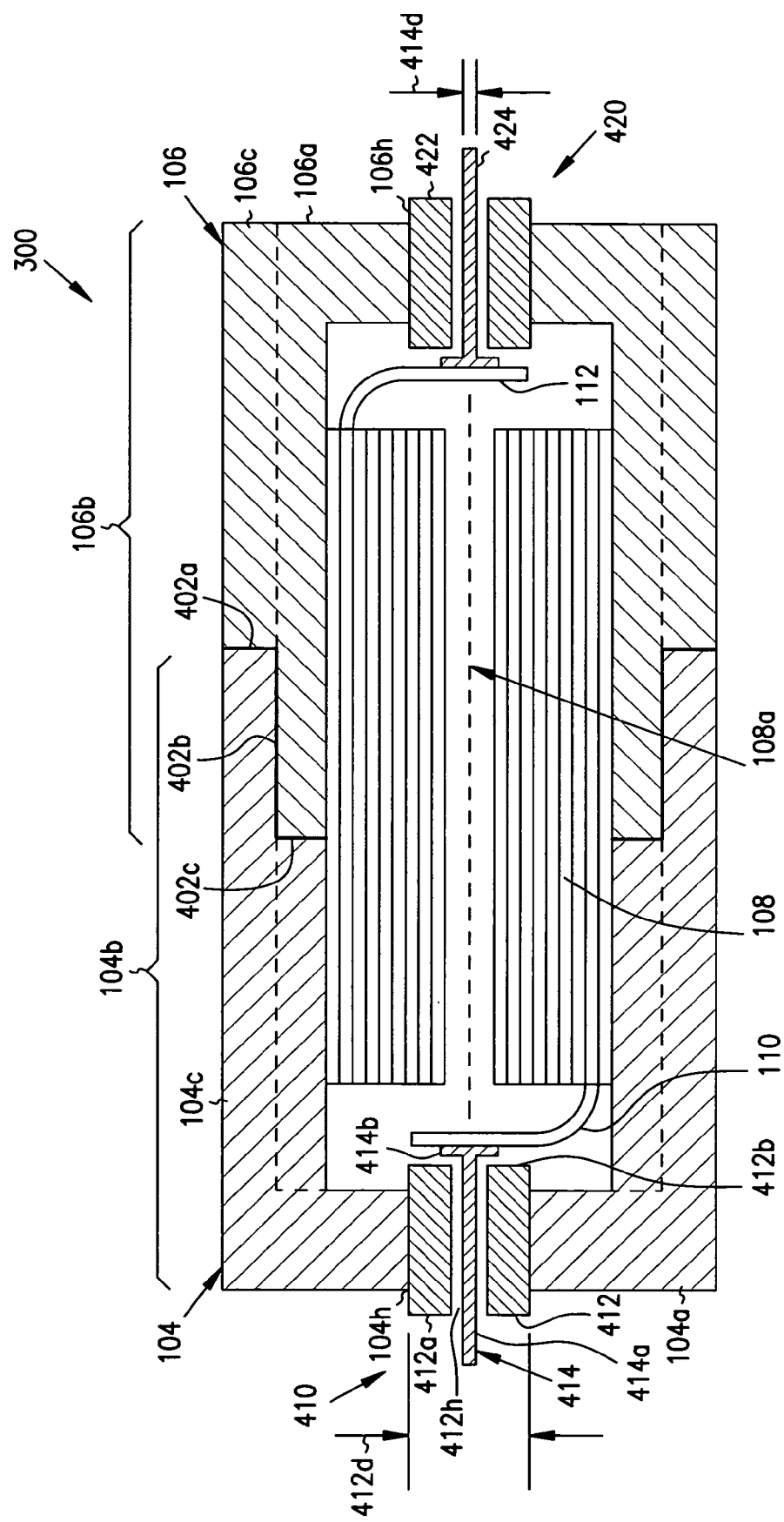
FIG. 4 is a cross-sectional view of capacitor 300 taken along line 4—4 in FIG. 3.

Capacitive element 108 includes an anode, a cathode, one or more inner separators, and two or more outer separators. The one or more inner separators are sandwiched between the anode and the cathode, and the resulting anode-separator-cathode sandwich is itself sandwiched between the outer separators. In the exemplary embodiment, the anode comprises three etched foils; the cathode comprises a single etched foil; and the separators comprise electrolyte-impregnated kraft paper. Exemplary foil materials include aluminum, tantalum, hafnium, niobium, titanium, zirconium, and combinations of these metals, and exemplary foil structures include core-etched, tunnel-etched, and perforated-core-etched foils. FIGS. 3 and 4 show an exemplary capacitor 300, which also embodies teachings of the present invention. Specifically, FIG. 3 shows a perspective view of capacitor 300, and FIG. 4 shows a cross-section of the capacitor taken along line 4—4.

In particular, capacitor 300, which is similar in many respects to capacitor 100 in FIGS. 1 and 2, includes cylindrical endcaps 104 and 106, cylindrical capacitive element 108, anode tab 110, and cathode tab 112. For sake of brevity, these aspects of capacitor 300 will be redescribed only where appropriate to highlight certain differences between the two exemplary embodiments.

Unlike capacitor 100, capacitor 300 omits tubular section 102, by forming a conductive interface 402 between endcaps 104 and 106. Endcaps 104 and 106 include respective planar end portions 104a and 106a and respective annular or tubular portions 104b and 106b. Tubular portions 104b include an interior annular shoulder 104c which mates with a complementary exterior annular shoulder 106c of tubular portion 106b, forming interface 402.

The exemplary embodiment seals an exterior portion 402a of the interface with an adhesive, such as an epoxy, or with a circumferential weld. Other embodiments, however, form middle portion 402b of the interface with threads on corresponding portions of tubular portions 104b and 106b. Still other embodiments omit annular shoulders 104c and 106c, welding, gluing, and or screwing tubular portions 104b and 106b together. Embodiments that omit shoulders 104c and 106c lack portions 402a and 402b of interface 402.

Planar end portions 104a and 106a include respective holes 104h and 106h for respective feedthrough assemblies 410 and 420. (Assemblies 410 and 420 are substantially identical in the exemplary embodiment, only assembly 410 is described here. However, some embodiments vary the assemblies appreciably still in keeping with one or more teachings of the invention.) Feedthrough assembly 410 includes a generally cylindrical insulative member 412 and a feedthrough conductor 414. Insulative member 412 includes an exterior face 412a, an interior face 412b, and a hole 412h which extends from face 412a to face 412b. Insulative member 412 has an exterior diameter (or more generally dimension) 412d for establishing an interference fit with hole 104h. In embodiments that construct insulative member 412 from glass or ceramic, the insulative member is secured in place by brazing the insulative member to the perimeter of hole 104h. (Some other embodiments weld a short metallic collar or sleeve to the case around the hole, insert the insulative member into the sleeve, and braze the insulative member to the sleeve and/or the feedthrough conductor. The sleeve can be made of aluminum or other metal compatible with the capacitor.)

Extending through hole 104h is a longitudinal shank portion 414a of feedthrough conductor 414. Shank portion 414a has a diameter or dimension 414d. Conductor 414a also has an integral disk-shaped head portion 414b which abuts interior face 412b of insulative member 412. An opposite side of head portion 414b is welded to anode tab 110, electrically coupling the feedthrough conductor to one or more anodes in capacitive element 108.

The exemplary embodiments forms insulative member 412 from glass, plastic, epoxy, or rubber and feedthrough conductor 414 from aluminum or other conductive material compatible with capacitive element 108. Additionally, it may be possible to size hole 104h, insulative member 412, hole 412h, and feedthrough conductor diameter 414d to cooperate with each other in establishing the interference fit between hole 104h and insulative member 412. Other embodiments epoxy the insulative member in place. Other embodiments mount the insulative member within hole 104h and apply an epoxy or other adhesive to secure and seal it in place. Still other embodiments mount the insulative member in a separate annular ring or collar having a flange, mount the annular ring into hole 104h and weld or braze the flange to planar portion 104a of the endcap.

Figure 5:
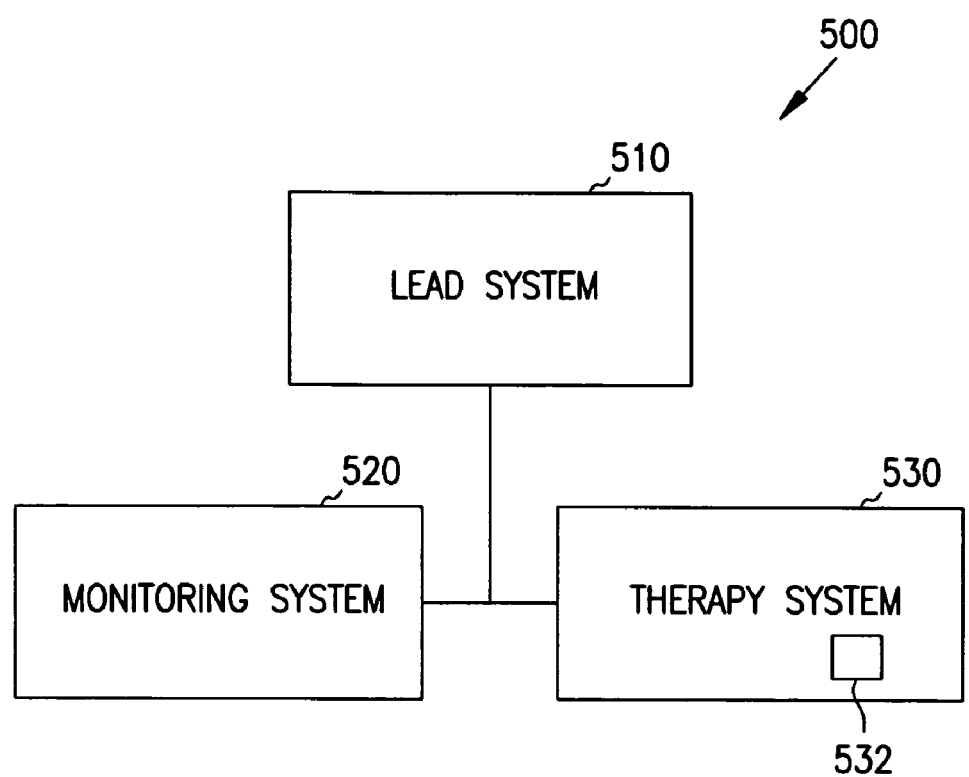
FIG. 5 is a block diagram of an exemplary implantable heart monitor 500 which includes one or more electrolytic capacitors 532 embodying teachings of the present invention.

FIG. 5 shows further details of the remaining portions of implantable heart monitor 500. Specifically, monitor 500 includes a lead system 510, which after implantation electrically contact strategic portions of a patient's heart, a monitoring circuit 520 for monitoring heart activity through one or more of the leads of lead system 510, and a therapy circuit 530 which includes one or more capacitors 532, each of which incorporates one or more teachings of capacitor 100 and/or 300. Monitor 500 operates according to well known and understood principles to perform defibrillation, cardioversion, pacing, and/or other therapeutic functions.

In addition to implantable defibrillators, congestive-heart-failure devices, and other cardiac rhythm management devices, such as pacemakers, the innovations of capacitor 100 can be incorporated into photographic flash equipment. Indeed, these innovations are pertinent to any application where compact, high-energy capacitors are desirable.

CONCLUSION

In furtherance of the art, the inventors have devised unique wet electrolytic capacitors for use in implantable heart monitors. One exemplary capacitor includes two conductive endcaps at opposite ends of its capacitive elements, instead of two upright terminals at one end, thereby allowing reduction in the height or volume of the capacitor and/or increases in the dimensions of other components, such as aluminum foils. Another exemplary capacitor includes two feedthrough assemblies at opposite ends of the wound capacitive element to also facilitate reduction in the height or volume of the capacitor or increase in its energy-storage density.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

The invention claimed is:

1. A wet electrolytic capacitor comprising:
a rolled capacitive element having first and second ends and including at least first and second metallic foils and at least one electrolyte impregnated separator between the foils;
a first conductive endcap electrically coupled to the first metallic foil and having a generally concave surface at least partially enclosing the first end of the rolled capacitive element;
a second conductive endcap electrically coupled to the second metallic foil and having a generally concave surface at least partially enclosing the second end of the rolled capacitive element; and
an insulative tube encircling a portion of the rolled capacitive element between the first and second ends of the element, with the insulative tube having a first end abutting the first conductive endcap and a second end abutting the second conductive endcap.

2. The capacitor of claim 1, wherein the first and second endcaps include respective first and second tubular portions which enclose respective portions of the rolled capacitive element.

3. The capacitor of claim 1, wherein each metallic foil consists essentially of aluminum.

4. The capacitor of claim 1, wherein each generally concave surface is substantially hemispherical.

5. A wet electrolytic capacitor comprising:
a rolled capacitive element having first and second ends and including at least first and second metallic foils and at least one electrolyte impregnated separator between the foils;
a first conductive endcap having a generally concave surface at least partially enclosing the first end of the rolled capacitive element;
a second conductive endcap having a generally concave surface at least partially enclosing the second end of the rolled capacitive element, with the second conductive endcap electrically isolated from the first conductive endcap; and
an insulative tube encircling a portion of the rolled capacitive element between the first and second ends of the element, with the insulative tube having a first end abutting the first conductive endcap and a second end abutting the second conductive endcap.

6. The capacitor of claim 5, wherein the first and second endcaps include respective first and second tubular portions which surround respective portions of the rolled capacitive element.

7. The capacitor of claim 5 wherein each metallic foil consists essentially of aluminum.

8. The capacitor of claim 5 wherein each generally concave surface is substantially hemispherical.

9. The capacitor of claim 5, wherein the first and second endcaps include respective first and second tubular portions which surround respective portions of the rolled capacitive element.

10. A wet electrolytic capacitor comprising:
a rolled capacitive element, the capacitive element including at least first and second metallic foils and at least one electrolyte impregnated separator between the foils;
first and second conductive endcaps, with each endcap having a concave surface confronting a respective end of the rolled capacitive element; and
an insulative tube having a first end abutting the first conductive endcap, a second end abutting the second conductive endcap, and a central insulative portion which is between the first and second ends and which surrounds a portion of the rolled capacitive element.

11. The capacitor of claim 10, wherein the concave surface of each endcap at least partially encloses the respective end.

12. The capacitor of claim 10, wherein the first and second endcaps include respective first and second tubular portions which encircle respective portions of the rolled capacitive element.

13. The capacitor of claim 10, wherein the first conductive endcap is electrically coupled to the second conductive endcap.

14. The capacitor of claim 10
wherein the first and second endcaps include respective first and second holes; and
wherein the capacitor further comprises:
a first feedthrough conductor extending through the first hole and electrically coupled to the first metallic foil; and
a second feedthrough conductor extending through the second hole and electrically coupled to the second metallic foil.

15. A wet electrolytic capacitor comprising:
a capacitive element having one or more metallic foils, with an anode tab electrically coupled to one or more of the metallic foils, and a cathode tab electrically coupled to one or more of the metallic foils;
a tubular housing portion surrounding at least a central portion of the capacitive element;
first and second endcaps, with the first endcap engaged with a first end portion of the tubular housing portion to contain a corresponding end portion of the capacitive element and the second end cap engaged with a second end portion of the tubular housing portion to contain a corresponding end portion of the capacitive element.

16. The capacitor of claim 15, wherein the capacitive element has a cylindrical form and the tubular housing portion has a cylindrical form.

17. The capacitor of claim 16, wherein the tubular housing portion is formed of a non-conductive material.

18. The capacitor of claim 17, wherein the non-conductive material is a ceramic, a polymer, or a plastic.

19. The capacitor of claim 15, wherein each endcap is formed of diecast or machined aluminum or other conductive metal compatible with the capacitive element.

20. The capacitor of claim 15, wherein each endcap has a cup-like structure comprising a generally planar end portion that confronts the corresponding end portion of the capacitive element and an adjoining tubular portion that surrounds the corresponding end portion of the capacitive element.

21. The capacitor of claim 15, wherein the tubular housing portion and each endcap are engaged to define a compound butt and lap joint.

22. The capacitor of claim 15, wherein the tubular housing portion and each endcap are threaded together.

23. The capacitor of claim 15, wherein the tubular housing portion and each endcap are adhered together.

24. The capacitor of claim 15, wherein the anode tab contacts an interior surface of the first endcap, and the cathode tab contacts an interior surface of the second endcap.

25. The capacitor of claim 24, wherein the anode tab and the cathode tab are attached respectively to the interior surfaces of the first and second endcaps using a conductive adhesive.

26. The capacitor of claim 15, wherein the capacitive element comprises an anode, with the anode comprising at least three etched foils.

27. The capacitor of claim 15, wherein the capacitive element comprises a plurality of metallic foils, with each foil comprising tantalum, hafnium, niobium, titanium, or zirconium and having a core-etched, tunnel-etched, or perforated-core-etched structure.

28. The capacitor of claim 15, wherein each endcap includes means for feeding a conductor through to the capacitive element.

* * * * *

UNITED STATES PATENT AND TRADEMARK OFFICE
CERTIFICATE OF CORRECTION

PATENT NO. : 7,190,569 B2 Page 1 of 1
APPLICATION NO. : 10/736209
DATED : March 13, 2007
INVENTOR(S) : O'Phelan et al.

It is certified that error appears in the above-identified patent and that said Letters Patent is hereby corrected as shown below:

Title page, Item (56), under "U.S. Patent Documents", in column 1, line 1, delete "1,747,486" and insert -- 1,474,486 --, therefor.

Title page, Item (56), under "U.S. Patent Documents", in column 1, line 3, delete "3,555,326" and insert -- 2,555,326 --, therefor.

Title page, Item (56), under "U.S. Patent Documents", in column 2, line 4, after "Thomas" insert -- et al. --.

In column 6, line 44, in Claim 14, after "Claim 10" insert -- : --.

Signed and Sealed this

First Day of July, 2008

JON W. DUDAS
*Director of the United States Patent and Trademark Office*